United States Patent [19]
Prashad et al.

[11] Patent Number: 5,596,094
[45] Date of Patent: Jan. 21, 1997

[54] PROCESS FOR PREPARING 2'-O-ALKYL ADENOSINE DERIVATIVES

[75] Inventors: Mahavir Prashad, Hopatcong; Prasad K. Kapa, Parsippany, both of N.J.

[73] Assignee: Sandoz Ltd., Basle, Switzerland

[21] Appl. No.: 485,595

[22] Filed: Jun. 7, 1995

Related U.S. Application Data

[63] Continuation-in-part of Ser. No. 249,914, May 26, 1994, abandoned.

[51] Int. Cl.$^6$ .......................... C07H 1/00; C07H 19/167
[52] U.S. Cl. ........................................ 536/55.3; 536/27.6
[58] Field of Search ........................ 536/55.3, 27.6

[56] References Cited

U.S. PATENT DOCUMENTS

| | | | |
|---|---|---|---|
| 4,843,066 | 6/1989 | Yamada et al. | 514/46 |
| 4,985,409 | 1/1991 | Yamada et al. | 514/46 |

OTHER PUBLICATIONS

Manoharan et al. Tetrahedron Letters 32(49):7/71–7/74, 1991.
Wagner et al Nucl. Acids Res. 19(21):5965–5971, 1991.
Sproat et al. Nucl. Acids Res. 19(4):733–738, 1991.
Robins et al. Can. J. Chem. 59:3360–3364, 1981.
Merz, Andreas Angew. Chem. 85(19):868–869, 1973.

*Primary Examiner*—Gary L. Kunz
*Attorney, Agent, or Firm*—Robert S. Honor; Melvyn M. Kassenoff; Thomas O. McGovern

[57] ABSTRACT

A process for alkylating the 2'-OH of $N^6$-modified adenosine comprising the reacting of an unprotected $N^6$-alkyl adenosine with dimethyl sulfate and tetrabutylammonium hydrogen sulfate in a non-polar solvent, preferably dichloromethane, and 5% sodium hydroxide. The products of the reaction are useful as anti-diabetic, hypolipidemic, and analgesic agents.

8 Claims, No Drawings

PROCESS FOR PREPARING 2'-O-ALKYL ADENOSINE DERIVATIVES

This application is a continuation-in-part of U.S. patent application Ser. No. 08/249,914, filed May 26, 1994, now abandoned.

This invention relates to processes for preparing $N^6$-substituted adenosine derivatives, which are useful as pharmaceutical agents. More particularly, this invention concerns processes for preparing $N^6$-cycloalkyl and aryl substituted-2'-alkoxy adenosine derivatives, which are useful as antihypertensive, anti-diabetic and hypolipidemic agents.

The compounds prepared by the process of this invention may be represented by the following structural formula:

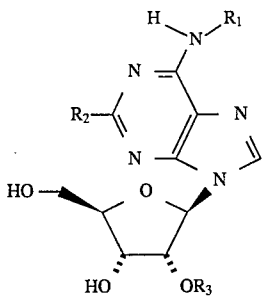

I wherein $R_1$ is hydrogen; $(C_{1-4})$alkyl; allyl; methallyl; a straight-chain or branched $(C_{3-7})$alkynyl; $(C_{3-8})$cycloalkyl; phenyl mono-or independently disubstituted by halogen having an atomic number of 9 to 35, $(C_{1-4})$alkyl, $(C_{1-4})$alkoxy, or $CF_3$; or phenyl-$(C_{1-4})$alkyl wherein the phenyl ring is unsubstituted or mono- or independently di-substituted by halogen having an atomic number of 9 to 35, $(C_{1-4})$alkyl, $(C_{1-4})$alkoxy or $CF_3$; $(C_{1-4})$alkyl substituted by at least two phenyl groups, a bicycloalkyl group, a naphthyl$(C_{1-4})$alkyl group, an acenaphthylenyl$(C_{1-4})$alkyl-group or a group of formula

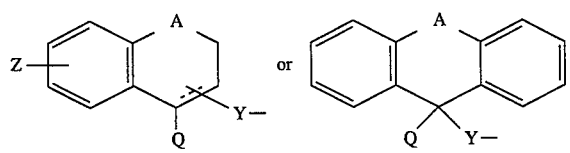

wherein

Z=hydrogen or a $(C_{1-4})$ alkoxy group,

Q=hydrogen,

A=—$CH_2$—, —O—, —S— or a direct bond,

Y=—$(CH_2)_n$— or a direct bond, n=1–3 and the broken line represents an optional bond, $R_2$ is hydrogen, $(C_{1-4})$alkyl, amino, $(C_{3-5})$cycloalkyl or halogen with an atomic number of 9 to 35 and $R_3$ is $(C_{1-4})$alkyl, or pharmaceutically acceptable salts thereof.

The preferred compounds of the invention have the formula:

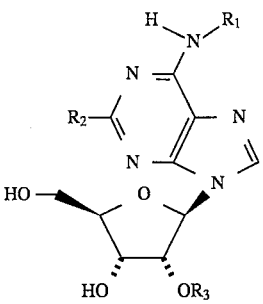

I wherein $R_1$ is $(C_{3-8})$cycloalkyl, $R_2$ is hydrogen or $(C_{1-4})$alkyl, and $R_3$ is $(C_{1-4})$alkyl.

Substituent $R_1$ is preferably cyclopentyl or especially cyclohexyl. Substituent $R_2$ is preferably hydrogen and $R_3$ is preferably methyl.

The compounds of formula I and their use in the treatment of hypertension are described in U.S. Pat. No. 4,843,066 and U.S. Pat. No. 4,985,409. Their preparation involves six steps, which include the preparation of 2',3',5'-triacetylinosine; chlorination and hydrolysis to 6-chloro-9-β-D-ribofuranosyl-9H-purine; protection of the 3'-O- and 5'-O-positions with tetraisopropyldisiloxane (TIPDS-$CL_2$); 2'-O-alkylation and purification by silica gel chromatography; deprotection of the 3'-O- and 5'-O-positions; and reaction with $R_1NH_2$ and recrystalization to obtain the compound of formula I.

It has now been found that the compounds of formula I can be prepared in good yields and purity without the need for 3'-O- and 5'-O-disiloxane protection and deprotection or for silica gel chromatography. Applicants have also found that the inosine-2',3',5'-triacetate starting material of the prior art process may be advantageously replaced with the lipophilic inosine-2',3',5'-tripropionate, which permits the doubling of throughput and the elimination of the undesirable pyridine solvent.

In the present invention the compound of formula (I) are prepared under phase transfer catalysis conditions in accordance with the following reaction scheme:

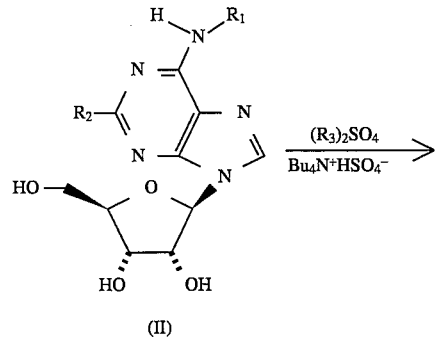

(II)

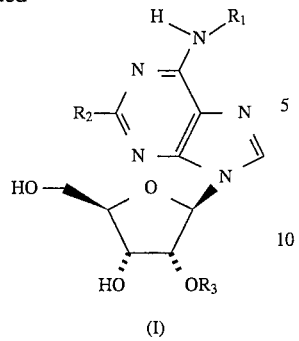

(I)

where $R_1$, $R_2$ and $R_3$ are as defined above.

The compounds of formula (I) are prepared by reacting a basic aqueous solution of a compound of formula (II) with a di-($C_{1-4}$)alkyl sulfate in the presence of tetrabutylammonium hydrogen sulfate and a water immiscible or essentially water immiscible solvent. The base used to prepare the basic aqueous solution is preferably an alkali metal hydroxide, such as sodium hydroxide or potassium hydroxide. The solvent can be any water-immiscible or essentially immiscible solvent in which the compound of formula (I) is soluble, such as tert-amyl alcohol and methylene dichloride. It is also preferred that the reaction be run at temperatures between about −20° C. to about 30° C., in particular, room temperature. The time of the reaction is not critical, but it is preferably carried out over a period of from about 5 to 10 hours, especially about 7 to 8 hours. The crude compound of formula (I) is isolated by evaporation followed by stirring with a 1:1 mixture of water and inert solvent, preferably toluene, at room temperature for 5 to 7 hours, then filtering and drying. Pure compound is obtained by fractional crystallization, preferably by: 1) recrystalization from an inert solvent, such as toluene, by dissolving the crude compound in the solvent at 80° C., heating at about 55° C. for approximately 1 hour, cooling to room temperature, seeding with pure compound and filtering; 2) repeating the recrystallization procedure of 1) but heating at about 65° C. before cooling to room temperature; and 3) recrystallizing from 100% ethyl alcohol by dissolving at reflux, diluting with water, seeding cooling, then filtering and drying.

Many of the compounds of formula (II) are known and may be prepared by methods described in the literature such as the aforementioned U.S. Pat. No. 4,843,066 and U.S. Pat. No. 4,985,409. The compounds of formula (II) may also be prepared advantageously, as indicated above, in accordance with the following preferred reaction scheme:

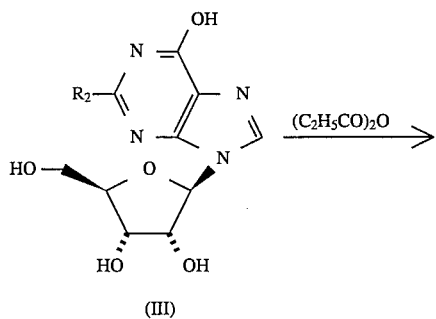

(III)

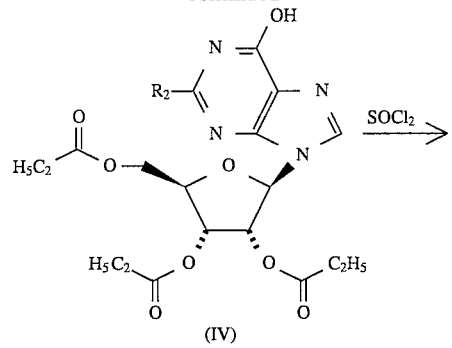

(V)

where $R_1$ and $R_2$ are as defined above.

The compounds of formula (II) are prepared by acylating an inosine of formula (III) with propionic anhydride to form the 2'-O-,3'-O-,5'-O-protected compound of formula (IV); halogenating the compound of formula (IV) with thionyl chloride to form the intermediate of formula (V); and simultaneously aminating and hydrolyzing the compound of formula (V). Acylation of an inosine is preferably carried out in a mixture of toluene, tributylamine, and 4-dimethylaminopyridine at a temperature of from 100° to 110° C. over a period of 4 to 5 hours. The compound of formula (IV) is isolated by precipitation with heptane. Halogenation of the compound of formula (IV) is preferably carried out in a mixture of toluene and N,N-dimethylformamide at a temperature of from about 60° to 70° C. over a period of 3 to 4 hours, and the solution of the compound of formula (V) is used as is after washing with water and brine. Amination and simultaneous hydrolysis of the intermediate of formula (V) is preferably effected by adding the amine $R_1NH_2$ and reacting at a temperature of from 100° to 110° C. over a period of 15 to 20 hours. The compound of formula (II) is isolated by filtration at room temperature and purified by recrystallization.

The antihypertension activity of the compounds are described in detail in U.S. Pat. No. 4,843,066 and U.S. Pat. No. 4,985,409. The following tests illustrate the anti-diabetic and hypolipidemic activity of the compounds:

1) Lipid and Glucose in Normal 18 hr Fasted Rats

The rats, 2 to 3 months of age, weighing 250 grams are kept in a room at a controlled ambient temperature of 22° C. and a 12/12 hour light/dark cycle for seven days. Purina Rat Chow and water are available ad libitum, except during fasting. Following an 18 hour fast, rats (5/group) are given test compounds by garage in CMC (0.5% carboxymethylcellulose with 0.2% Tween 80).

The animals receive 1.0 ml/100 g body wt. Three hours after administration, the rats are anesthetized with $CO_2$; and blood is collected via cardiac puncture. Sera are collected and used for glucose, free fatty acid and β-hydroxybutyrate determination. Free fatty acids are measured by acyl-COA Synthetase colorimetric enzyme assay (Wako Pure Chemical Industries NEFAC Kit, Osaka, Japan); glucose is measured by the glucose oxidase method (YSI Model 27 or 2700, Yellow Spring, Ohio); and β-hydroxybutyrate is assayed with a β-hydroxybutyrate dehydrogenase-linked enzyme assay (Sigma Kit 310-UV, St. Louis, Mo.). The compounds are active in lowering free fatty acid levels at a dose of from about 10 to about 500 µg/kg. For the title compound of Example 1, the $ED_{50}$ for lowering free fatty acids (the primary result of the effect on adipocytes) is 20–25 µg/kg at 2 hr post dose. This results in a dose dependent decrease in β-hydroxybutyrate and blood glucose levels.

2) Effects in Non-Insulin Dependent Diabetic (NIDD) Rats

In the NIDD screen test, the rats (200–220 g) are fed a high fat diet ad libitum. At fed state, 40 mg of streptozotocin/kg of body weight are injected via the tail vein. Five days later, those rats are considered to be diabetic which have fed blood glucose of greater than 200 mg/dl and, following an overnight fast, when given an oral glucose tolerance test, have blood glucose of 40 to 80 mg/dl three hours after the test. Four days later, animals are used in the screen, if fed blood glucose levels are greater than 180 mg/dl. Blood glucose is determined with a YSI Glucose Analyzer. The chronic screen test is carried out as follows:

On Day 1, food is removed from rats at 9:00 A.M.; and after an initial blood glucose reading is taken via the tip of the tail, vehicle (CMC control) or compound in vehicle (9 rats/treatment) is administered orally. Two and six hours later blood glucose level is measured; and immediately thereafter the rats are refed. The same rats are given either vehicle or drug once a day for 11 consecutive days. Blood glucose is determined at 0 hour and after 2 and 6-hour fasts post-dosing on days 4, 8, and 11. The compounds of the invention, for example the title compound of Example 1 at 100 µg/kg, produce a significant reduction in plasma free acids, which produce a significant decrease in blood glucose.

3) Dyslipidemias characterized by elevated serum triglycerides

Several studies have shown a positive correlation between serum triglyceride levels (and an associated decreased HDL cholesterol level) and the risk for coronary heart disease (CHD) (Grundy, in Cholesterol and Atherosclerosis: Diagnosis and Treatment, Lippincott, Philadelphia (1990)). The value of reducing elevated triglyceride levels as an approach to reducing the risk of CHD emerged from the Helsinki Heart Study where, following treatment with gemfibrozil, the greatest reduction in serious coronary events occured in Type IIB hyperlipidemic patients in whom both LDL-cholesterol and total serum triglycerides are elevated and HDL cholesterol levels are generally reduced. The compounds of the invention are active in the Rhesus monkey at doses from about 0.03 to 30 (e.g. 0.1 to 30) mg/kg i.v. and 0.1 to 100 (e.g. 0.1 to 10) mg/kg p.o.

The compounds of formula I are also useful as analgesics, for example for the treatment of pain, such as acute or chronic pain. The analgesic activity of the compounds of the formula I are indicated by their analgesic activity in standard animal tests, e.g. in inflammatory and neuropathic models in reducing persistent inflammatory mechanical hyperanalgesia [(tests a) and b) below] and persistent neuropathic thermal hyperalgesia [test c) below] indicative of chronic neuropathic pain.

Test a) Freund's adjuvant-induced hyperalgesia

Rats are injected intra-articularly in one knee joint with Freund's complete adjuvant (100 microlitres). The load that the rat will tolerate on that leg decreases and remains depressed for up to 5 days. This effect is indicative of mechanical hyperalgesia, and is responsive to NSAID's and opiates. The compounds of the formula I are administered by injection and preferably orally at doses of from about 3 to 60 microgram/kg animal body eight. The increased load tolerated on the injected side is measured to determine the reversal of hyperalgesia. The compound of Example 1 below shows particularly interesting activity on p.o. administration from about 3 to about 60 microgram/kg with a duration of action about 1 hour. There is no significant difference in response between the doses of 3, 30 and 60 microgram/kg suggesting that the maximum effect had been reached in the range 3 to 30 microgram/kg.

Test b) Turpentine-induced mechanical hyperalgesia

A local intra-plantar injection of turpentine/paraffin in rat paw (left hind) results in a local inflammatory response and a reduction in the withdrawal threshold (cut-off threshold 340 g) for a mechanical stimulus (paw pressure). The compounds of formula I are active at doses from about 1 to 100 microgram/kg p.o. or s.c. administered three days after the injection, further threshold readings being taken 1 and 3 hours later. The compound of Example 1 shows significant activity at doses of 30 and 60 microgram/kg orally, with the maximum effect at 30 microgram/kg. Morphine has an $ED_{50}$ value of 1.2 mg/kg s.c. in this test.

Test c) Neuropathic thermal hyperalgesia
(according to the principles of Z. Seltzer et al.,
Pain, 1990, 43, 205–218)

Unilateral partial ligation of the sciatic nerve eliminates fibres throughout the innervation of a paw of a rat. The rats develop hyperalgesia to mechanical and thermal stimuli and allodynia of the partially denervated paw without the induction of autotomy. The animals are placed in a perspex box on a thin glass plate and a ramp-shaped heat stimulus is applied to the plantar surface of a paw. Latency to paw withdrawal is measured. The compounds of the formula I are active at doses from about 1 to about 100 microgram/kg injection (s.c. or preferably orally), administered 12 to 15 days after nerve ligation. The compound of Example 1 is particularly active against thermal hyperalgesia and shows significant activity at doses of 30 and 60 microgram/kg, with the maximum effect at 30 microgram/kg. The $ED_{50}$ is about 60 microgram/kg p.o. Morphine has an $ED_{50}$ of around 3 mg/kg in this test when administered subcutaneously.

The compounds of the invention are therefore useful as analgesics, e.g. against acute or chronie pain, for example acute pain associated with tissue damage and inflammation (e.g. post operative pain, burn pain, injuries, etc.) chronic inflammatory pain (e.g. arthritis) and chronic neuropathic pain (e.g. diabetic neuropathy, post-herpetic neuralgia, multiple sclerosis, causalgia, etc.). The doses of the compound used will, of course, vary depending on the compound employed, the seriousness of the disorders, the host, the weight, the mode of administration and the relative efficacy of the compound. However, in general, satisfactory results in animals are obtained at 3 daily doses from about 1 to about 100 microgram/kg animal body weight, e.g. 3 to 60, in particular 10 to 60, microgram/kg. In larger mammals, for example humans, an indicated daily dose is from about 0.1 to about 10 mg, conveniently administered in unit doses from about 0.02 to about 5 mg, and such unit doses may be administered more than once a day, for example 2, 3, 4, 5 or 6 times a day, but preferably 1 or 2 times per day.

In test a) above, the NSAID ibuprofen has an $ED_{50}$ of about 4 mg/kg p.o. and indomethacin 13 mg/kg p.o. The compound of Example 1 is about 300 times more active. For this compound, the preferred dose range is from about 0.1 mg/day to about 10 mg/day, e.g. 3–30 microgram/kg for a 70 kg adult, depending on the severity of the indication(s) and frequency of administration.

Example 1

$N^6$-cyclohexyl-2'-O-methyladenosine

Step A. Inosine-2',3',5'-tripropionate

A mixture of 271.2 g of inosine, 966 ml of tributylamine, 3.30 g of 4-dimethylaminopyridine and 600 ml of toluene is heated to an internal temperature of 104°–105° C.; and over a period of 35 minutes, 453 ml of propionic anhydride are added at a rate which maintains the internal temperature between 104°–105° C. After stirring the mixture at this temperature for an additional 4 hours, the mixture is cooled to 5°–10° C. with an ice bath; and 1000 ml of heptane are added. The resulting suspension is stirred at room temperature (20°–22° C.) for 30 minutes and then filtered on a Buchner funnel. The solids are washed with a total of 450 ml of heptane in three equal portions of 150 ml each and dried at 45°–50° C. (25 mm Hg) overnight (14 hours) to yield 425.9 g of inosine-2',3',5'-tripropionate as a white solid. (MP 171°–172° C.; yield 96.5%).

Step B. $N^6$-cyclohexyladenosine

A mixture of 270.6 g of inosine-2',3',5'-tripropionate, 240 ml of N,N-dimethylformamide and 600 ml of toluene is heated to 65° C.; and over a period of 1 hour, 67.84 ml of thionyl chloride are added at a rate which maintains the internal temperature between 62°–65° C. The mixture is stirred at this temperature for an additional 2.5 hours and then cooled to 10° C. with an ice bath. After addition of 600 ml of water precooled to 10°–15° C. in an ice bath at a rate which maintains the temperature below 20° C., the organic layer is separated and washed with a total of 800 ml of 10% aqueous sodium chloride in four equal portions of 200 ml each. The organic layer containing crude 6-chloro-9-(2,3,5-tri-O-propionyl-β-ribofuranosyl)-9H-purine is added with stirring to 620 ml of cyclohexylamine heated to 105° C. over a period of 2 hours at a rate which maintains the internal temperature at 105° C. After this mixture is stirred at this temperature for an additional 17 hours, it is cooled to room temperature (25° C.) over approximately 2 hours with efficient stirring and then filtered in a Buchner funnel with suction. The solid containing $N^6$-cyclohexyladenosine and cyclohexylamine hydrochloride is washed with a total of 460 ml of toluene in four equal portions of 115 ml. each and transferred damp to a 5-liter flask equipped with a mechanical stirrer. After addition of 2 liters of aqueous saturated sodium bicarbonate solution and 2.5 liters of ethyl acetate, the mixture is stirred until all the solid dissolve (approximately 10–15 min.). The organic layer is separated; and the aqueous layer is extracted with 1.5 liters of ethyl acetate in two portions of 1 liter and 500 ml., respectively. The organic layers are combined and evaporated until about 3 liters of ethyl acetate (at 40° C., 100–200 mbar) is removed. To the residue, 500 ml. of heptane is added; and the resulting mixture is stirred for 30 minutes. The solids are separated on a Buchner funnel, and washed with a total of 300 ml of heptane in three equal portions of 100 ml each. The solids are then dried at 45°–50° C. (30–35 mbar) for approximately 3 hours to yield 148 g of crude $N^6$-cyclohexyladenosine as a white solid. This is transferred to a 1 liter round-bottomed flask equipped with a mechanical stirrer, and 175 ml. of 95% ethanol are added. The suspension is stirred for 15–20 min and 175 mL of tert-butyl ethyl ether are added. After stirring for 5 min, the suspension is cooled in an ice bath and stirred for an additional 15 minutes. This suspension is filtered in a Buchner funnel and washed with a total of 50 ml. of tert-butyl methyl ether in two equal portions of 25 ml. each. The solid is dried at 45°–50° C. (30–35 mbar) for 14 hours to yield 130 g of $N^6$-cyclohexyladenosine as a white solid (m.p. 185°–187° C.; yield 60.0%).

Step C. $N^6$-cyclohexyl-2'-O-methyladenosine

A suspension of 94.33 g of $N^6$-cyclohexyladenosine and 720 g of 5% aqueous sodium hydroxide are stirred at room temperature (24°–25° C.) until all of the solids are dissolved (approximately 5 min.). Using an addition funnel, 850 ml. of dichloromethane and 5.5 g of tetrabutylammonium hydrogen sulfate are added followed by 61.3 g of dimethyl sulfate over 5–10 minutes, while maintaining the internal temperature at 24°–25° C. The addition funnel is washed with an additional 50 ml of dichloromethane which is added to the reaction vessel. After stirring the biphasic mixture at 24°–25° C. (internal temperature) for 7.5 hours the organic layer is separated and evaporated at 40° C.,(270–290 mbar) until no further solvent distills. The residue is dissolved in 200 ml of toluene and evaporated at 45°–50° C. (30 mm Hg) until again no further solvent distills.

A mixture of the crude material above and 2470 ml of toluene is stirred at room temperature for 10 minutes and then 2470 ml of water are added over a period of 22 min. The resulting suspension is stirred at room temperature for an additional 6 hours and solids are collected by filtration in a Buchner funnel with suction. After washing the solids with 114 ml of toluene and a total of 285 ml. of water in three equal portions of 95 ml each, the solids are dried at 48°–50° C. (25 mm Hg) overnight (14 hours) to yield 53.0 g of a white solid. A suspension of this solid in 397 ml. of toluene is heated to 80° C. with stirring to form a clear solution, which is cooled to 56° C. over 45 min and seeded with 10 mg of pure product. The mixture is stirred at 55°–56° C. for 45 minutes and then cooled to room temperature over 1 hour. After stirring at this temperature for an additional 1 hour the solid are collected by filtration in a Buchner funnel with suction. The solids are washed with a total of 75 ml. of toluene in three equal portions of 25 ml. each to yield 60 g of a white solid. A suspension of this solid in 159 ml of toluene is again heated to 80° C., and the above seeding procedure is carried out at 65° to 66°. After filtration, the solids are washed with 42 ml. of toluene in three equal portions of 14 ml. each and dried at 48°–50° C. (25 mm Hg) overnight (14 hours) to yield 57.7 g of a white solid. The solid and 122 ml. of 100% ethanol are heated to reflux with stirring to obtain a clear solution, and 288 ml. of water pre-warmed to 55° C. are added over 25 minutes. The mixture is cooled to 55° C. and seeded with 20 mg of pure product. This mixture is cooled to room temperature over 1 hour and stirred at this temperature overnight (16 hours). The solids are collected by filtration in a Buchner funnel with suction and washed with a total of 57 ml. of 1:2.36 mixture (v/v) of 100% ethanol and water in three equal portions of 19 ml each. The solids are dried at room temperature (29 mm Hg) to yield 62.2 g of product as a white solid in 1.5 hydrate form (m.p. 88°–91° C.; yield 42.5%.

Example 2

Following the above procedure but using an equivalent amount of $N^6$-cyclopentyladenosine, there is obtained $N^6$-cyclopentyl-2-O-methyladenosine.

EXAMPLE 3

$N^6$-cyclohexyl-2-O-methyladenosine

A suspension of 94.33 g of $N^6$-cyclohexyladenosine and 720 g of 5% aqueous sodium hydroxide are stirred at room temperature (24°–25° C.) until all of the solids are dissolved (approximately 5–10 min.). Using an addition funnel, 850 ml. of tert-amyl alcohol and 5.5 g of tetrabutylammonium hydrogen sulfate are added followed by 91.95 g of dimethyl sulfate over 2 hours and 15 minutes, while maintaining the internal temperature between 24°–25° C. The addition funnel is washed with an additional 50 ml of tert-amyl alcohol, which is added to the reaction vessel. After stirring the biphasic mixture at 24°–25° C. (internal temperature) for 3.5 hours, 100 ml of 29.9% ammonium hydroxide is added; and the mixture is stirred at 24°–25° C. for an additional 2 hours. The organic layer is separated and evaporated at 40°–50° C.,(30–35 mbar) until no further solvent distills. The residue is dissolved in 200 ml of toluene and evaporated at 45°–50° C. (30 mm Hg) until again no further solvent distills.

A mixture of the crude material above and 2470 ml of toluene is stirred at room temperature for 10 minutes and then 2470 ml of water are added over a period of 22 min. The resulting suspension is stirred at room temperature for an additional 6 hours and solids are collected by filtration on a Buchner funnel with suction. After washing the solids with 114 ml of toluene and a total of 285 ml. of water in three equal portions of 95 ml each, the solids are dried at 48°–50° C. (25 mm Hg) overnight (14 hours) to yield 42.0 g of a white solid. A suspension of this solid in 315 ml. of toluene is heated to 80° C. with stirring to form a clear solution, which is then cooled to 56° C. over 45 min and seeded with 10 mg of pure $N^6$-cyclohexyl-2-O-methyladenosine. The mixture is stirred at 55°–56° C. for 45 minutes and then cooled to room temperature over 1 hour. After stirring at this temperature for an additional 1 hour, the solid are collected by filtration on a Buchner funnel with suction. The solids are washed with a total of 60 ml. of toluene in three equal portions of 20 ml. each to yield 45.2 g of a white solid. A suspension of this solid in 120 ml of toluene is again heated to 80° C., and the above seeding procedure is carried out at 65° to 66°. After filtration, the solids are washed with 33 ml. of toluene in three equal portions of 11 ml. each and dried at 48°–50° C. (25 mm Hg) overnight (14 hours) to yield 43.6 g of a white solid. The solid and 92.4 ml. of 100% ethanol are heated to reflux with stirring to obtain a clear solution, and 218 ml. of water pre-warmed to 55° C. are added over 25 minutes. The mixture is cooled to 55° C. and seeded with 20 mg of pure product. This mixture is cooled to room temperature over 1 hour and stirred at this temperature overnight (16 hours). The solids are collected by filtration on a Buchner funnel with suction and washed with a total of 42 ml. of 1:2.36 mixture (v/v) of 100% ethanol and water in three equal portions of 14 ml each. to obtain 34.4 g of white solids. The solids and 41.2 ml. of 100% ethanol are heated to reflux with stirring to obtain a clear solution, and 82.4 ml. of water pre-warmed to 55° C. are added over 15 minutes. The mixture is cooled to 49°–51° C. and seeded with 20 mg of pure product. This mixture is cooled to room temperature over 1 hour and stirred at this temperature for 2 hours. The solids are collected by filtration on a Buchner funnel with suction and washed with a total of 20 ml. of 1:2 mixture (v/v) of 100% ethanol and water in two equal portions of 10 ml each. The solids obtained are dried at room temperature (25–30 mm Hg) for 72 hours to yield 32.1 g of product as a white solid (m.p. 88°–91° C.; yield 30.45%; purity 98.40%).

What is claimed is:

1. A process for the preparation of a compound of the formula

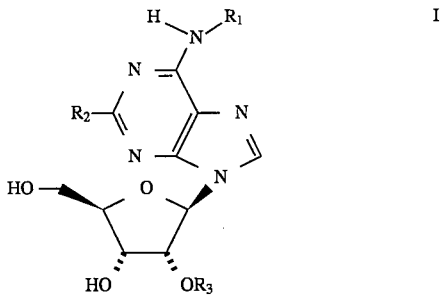

wherein $R_1$ is hydrogen; $(C_{1-4})$alkyl; allyl; methallyl; straight-chain or branched $(C_{3-7})$alkynyl; $(C_{3-8})$cycloalkyl; phenyl mono- or independently disubstituted by halogen having an atomic number of 9 to 35, $(C_{1-4})$alkyl, $(C_{1-4})$alkoxy or $CF_3$; or phenyl$(C_{1-4})$alkyl wherein the phenyl ring is unsubstituted or mono- or independently di-substituted by halogen having an atomic number of 9 to 35, $(C_{1-4})$alkyl, $(C_{1-4})$alkoxy or $CF_3$; $(C_{1-4})$ alkyl substituted by at least two phenyl groups, naphthyl $(C_{1-4})$alkyl, acenaphthylenyl $(C_{1-4})$)alkyl or a group of the formula

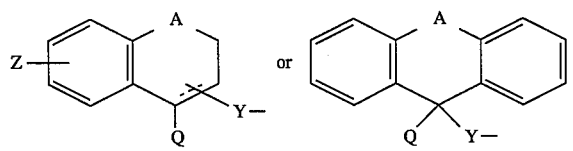

wherein

Z=hydrogen or $(C_{1-4})$alkoxy,

Q=hydrogen,

A=—$CH_2$—, —O—, —S— or a direct bond,

Y=—$(CH_2)_n$— or a direct bond, n=1–3, and the broken line represents an optional bond, $R_2$ is hydrogen, $(C_{1-4})$alkyl, amino, $(C_{3-5})$cycloalkyl or halogen with an atomic number of 9 to 35 and $R_3$ is $(C_{1-4})$ alkyl,
which comprises reacting a compound of the formula

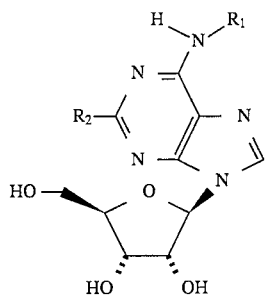   II with a basic solution of a compound of the formula

in the presence of tetrabutylammonium hydrogen sulfate and a water-immiscible or essentially water-immiscible solvent in which the compound of formula (I) is soluble, isolating the product, and purifying the product by recrystallization.

2. A process for the preparation of a compound of the formula

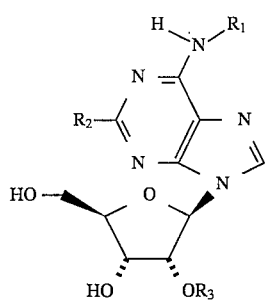   I wherein $R_1$ signifies $(C_{3-8})$cycloalkyl, $R_2$ is hydrogen or $(C_{1-4})$alkyl, and $R_3$ is $(C_{1-4})$alkyl, which comprises reacting a compound of the formula

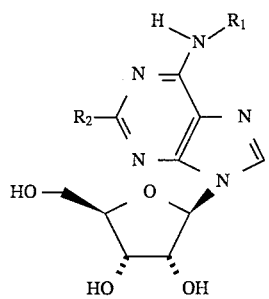   II with a basic solution of a compound of the formula

in the presence of tetrabutylammonium hydrogen sulfate and a water-immiscible or essentially water-immiscible solvent in which the compound of formula (I) is soluble, isolating the product, and purifying the product by recrystallization.

3. A process according to claim 2 in which the compound is N-cyclopentyl-2'-O-methyladenosine.

4. A process according to claim 2 in which the compound is N-cyclohexyl-2'-O-methyladenosine.

5. A process according to claim 2 in which the water-immiscible or essentially water-immiscible solvent is tert-amyl alcohol.

6. A process according to claim 1 in which the compound of formula (II) is prepared by acylating a compound of formula (III)

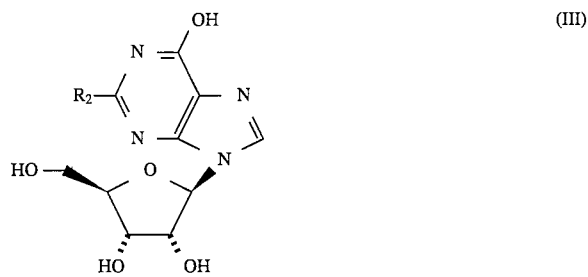   (III)

with propionic anhydride to obtain a compound of the formula (IV)

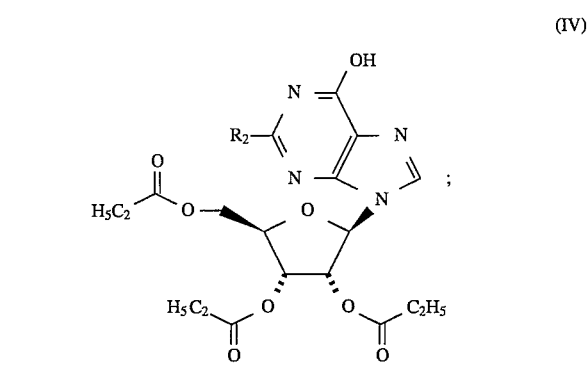   (IV)

reacting the compound of formula (IV) with thionyl chloride to obtain an intermediate of formula (V)

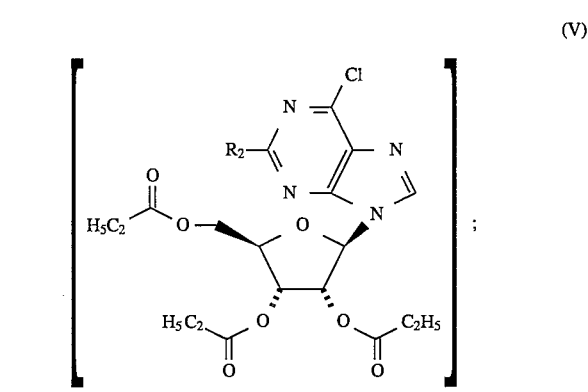   (V)

and simultaneously aminating the intermediate of formula (V) with $R_1NH_2$ and hydrolysing to obtain the compound of formula (II)

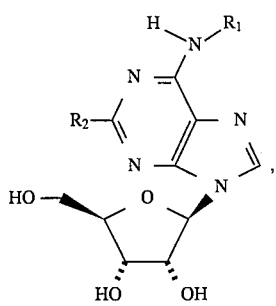 (II)

where $R_1$ and $R_2$ are as defined in claim 1.

7. A process according to claim 1 in which the product is purified by 1) recrystallization from an inert solvent by dissolving the product in the solvent at 80° C., heating at about 55° C. for approximately 1 hour, cooling to room temperature, seeding with pure product and filtering; 2) repeating the recrystallization procedure of 1) but heating at about 65° C. before cooling to room temperature; and 3) recrystallizing from 100% ethyl alcohol by dissolving at reflux, diluting with water, seeding, cooling, then filtering and drying.

8. A process according to claim 7 in which the solvent is toluene.

* * * * *